United States Patent
Veit et al.

(10) Patent No.: US 12,329,810 B2
(45) Date of Patent: Jun. 17, 2025

(54) PRODUCTION OF VIRUSES IN CONTINUOUSLY GROWING EPITHELIAL CELL LINES DERIVED FROM CHICKEN GUT

(71) Applicants: FREIE UNIVERSITÄT BERLIN, Berlin (DE); TENTAMUS PHARMA & MED DEUTSCHLAND GMBH, Karlsruhe (DE)

(72) Inventors: Michael Veit, Berlin (DE); Chris Tina Höfer, Berlin (DE); Wolfgang Rudy, Karlsruhe (DE)

(73) Assignees: FREIE UNIVERSITÄT BERLIN, Berlin (DE); TENTAMUS PHARMA & MED DEUTSCHLAND GMBH, Karlsruhe (DE)

( * ) Notice: Subject to any disclaimer, the term of this patent is extended or adjusted under 35 U.S.C. 154(b) by 940 days.

(21) Appl. No.: 17/426,043

(22) PCT Filed: Jan. 28, 2020

(86) PCT No.: PCT/EP2020/052061
§ 371 (c)(1),
(2) Date: Jul. 27, 2021

(87) PCT Pub. No.: WO2020/157076
PCT Pub. Date: Aug. 6, 2020

(65) Prior Publication Data
US 2022/0118078 A1   Apr. 21, 2022

(30) Foreign Application Priority Data
Jan. 28, 2019 (EP) .................... 19154039

(51) Int. Cl.
*A61K 39/145* (2006.01)
*A61K 39/00* (2006.01)
*C12N 5/071* (2010.01)
*C12N 7/00* (2006.01)

(52) U.S. Cl.
CPC .......... *A61K 39/145* (2013.01); *C12N 5/0679* (2013.01); *C12N 7/00* (2013.01); *A61K 39/00* (2013.01); *A61K 2039/552* (2013.01); *C12N 2760/16151* (2013.01)

(58) Field of Classification Search
CPC ............ A61K 39/145; A61K 2039/552; C12N 5/0679; C12N 7/00; C12N 2760/16151
See application file for complete search history.

(56) References Cited

FOREIGN PATENT DOCUMENTS

| | | | |
|---|---|---|---|
| EP | 2 080 768 A1 | 7/2009 | |
| JP | 2007510409 A * | 4/2007 | |
| NZ | 333006 A * | 8/2000 | ........... C12N 5/0602 |
| NZ | 333007 A * | 8/2000 | ........... C12N 5/0602 |
| WO | 02/089586 A1 | 11/2002 | |

OTHER PUBLICATIONS

JP 2007510409 A. Machine Translation. (Year: 2007).*
Kraus, Barbara, et al., "Avian cell line-Technology for large scale vaccine production" BMC Proceedings, vol. 5 No. 8 BioMed Central, Nov. 22, 2011.
Seitz, Claudius, et al. "High yields of influenza A virus in Madin-Darby canine kidney cells are promoted by an Insufficient interferon-induced antiviral state." Journal of General Virology 91 (7) (Mar. 31, 2010): 1754-1763.
Krammer et al., Advances in the Development of Influenza Virus Vaccines, Nature Reviews, Drug Discover, vol. 14, Mar. 2015.
Song et al., Advances in Novel Influenza Vaccines: a patent review, Journal of Microbiology, vol. 54, No. 6, pp. 403-412, 2016.

* cited by examiner

*Primary Examiner* — Janet L Andres
*Assistant Examiner* — Carey Alexander Stuart
(74) *Attorney, Agent, or Firm* — Maschoff Brennan

(57) ABSTRACT

It is provided a method for manufacturing viruses in an in vitro cell culture. The method comprising the following steps: providing a cell culture of avian epithelial cells chosen from at least one of the cell cultures deposited under deposition numbers DSM ACC3345, DSM ACC3346, DSM ACC3347, DSM ACC3348, DSM ACC3349 at Leibniz-Institut DSMZ-Deutsche Sammlung von Mikroorganismen and Zellkulturen GmbH on Dec. 12, 2018; infecting at least some of the cells in the cell culture with virus particles; incubating the cells for a first period of time; and recovering viruses produced by the cell culture from a supernatant of the cell culture.

13 Claims, 5 Drawing Sheets

PRODUCTION OF VIRUSES IN CONTINUOUSLY GROWING EPITHELIAL CELL LINES DERIVED FROM CHICKEN GUT

CROSS-REFERENCE TO A RELATED APPLICATION

This application is a National Phase Patent Application of International Patent Application Number PCT/EP2020/052061, filed on Jan. 28, 2020, which claims priority of European Patent Application Number 19 154 039.2, filed on Jan. 28, 2019.

BACKGROUND

The disclosure relates to a method for manufacturing viruses in an in vitro cell culture and to a method for manufacturing a vaccine.

Viruses to be used as vaccines against viral diseases like, e.g., against influenza are mainly produced in embryonated chicken eggs. For this purpose, viruses are injected into the allantoic cavity of the eggs. After 2 to 3 days, the allantoic cavity is opened, the allantoic fluid is removed and the viruses are prepared by ultracentrifugation. The viruses are then inactivated or attenuated and used as vaccines. Typically, viruses from one embryonic egg are required per human vaccination dose.

With the occurrence of the "bird flu" in 2005, the limitations of this old technique became clear. It could be difficult to get enough chicken eggs if whole poultry flocks are eliminated by a highly pathogenic virus. In addition, the H5N1 influenza virus, which is responsible for "bird flu", is difficult to reproduce in chicken eggs. Furthermore, vaccine production in chicken eggs takes too long to provide sufficient vaccines in time in the event of a new pandemic virus.

In 2009, e.g., the vaccine against "swine flu" could not be delivered until the second wave of infection was on its way. The long lead time for manufacturing the vaccine (approximately 6 months) is also a reason why, when a vaccine against seasonal influenza is administered, the vaccination viruses often no longer correspond to the viruses actually circulating.

Finally, people who are allergic to chicken protein cannot be vaccinated with viruses produced in chicken eggs.

Cell cultures are an alternative to the production of viruses in embryonated eggs. These can be multiplied on plastic shells and infected with viruses. Newly formed virus particles are released into the culture medium and can be prepared from it. In recent years, vaccines produced in Madin-Darby Canine Kidney (MDCK) cells have been approved, but are still rarely used. This cell line was selected because it is well characterized and has long been used in the laboratory to propagate influenza viruses.

An important criterion for a suitable cell line is that the cells release a large number of viruses. Each vaccination dose must contain a certain minimum amount of virus particles in order to trigger a sufficiently strong immune response. Cell culture is expensive due to the use of high-quality media and fetal calf serum as a growth factor. For economic reasons, as few cells as possible should produce as many viruses as possible.

Kraus, Barbara, et al. "Avian cell line-Technology for large scale vaccine production." *BMC Proceedings*. Vol. 5. No. 8. BioMed Central, 2011: P52 discloses the use of an avian cell line for large scale vaccine production.

WO 02/089586 A1 discloses a novel lung epithelial cell line, in particular a porcine lung epithelial cell line, supporting efficient high titer replication of viruses, in particular influenza viruses.

Seitz, Claudius, et al. "High yields of influenza A virus in Madin-Darby canine kidney cells are promoted by an insufficient interferon-induced antiviral state." *Journal of General Virology* 91 (7) (2010): 1754-1763 relates to influenza virus propagation in MDCK cells.

SUMMARY

It is an object underlying the proposed solution to provide a novel possibility to manufacture viruses suited for producing vaccines without using embryonated eggs with a higher efficiency than according to methods known from prior art.

According to a novel use of cells of an in vitro cell culture for the production of viruses the cells are continuously (permanently) growing avian cell lines derived from chicken gut (referred to in the following as avian epithelial cells). Under the provisions of the Budapest Treaty on the International Recognition of the Deposit of Microorganisms for the Purpose of Patent Procedure, Applicant has deposited cell cultures of avian epithelial cells at Leibniz-Institut DSMZ-Deutsche Sammlung von Mikroorganismen und Zellkulturen GmbH (Leibniz Institute DSMZ-German Collection of Microorganisms and Cell Cultures) on Dec. 12, 2018 under the accession numbers DSM ACC3345, DSM ACC3346, DSM ACC3347, DSM ACC3348, and DSM ACC3349.

When testing different cell lines, it turned out that these specific avian epithelial cells are particularly appropriate to produce a significantly higher number of viruses than MDCK cells used according to prior art techniques for producing influenza viruses in cell culture. Thus, by using the above-mentioned cell cultures, it was possible to produce up to 10 times more viruses in the same time period in the same amount of cells. Thus, by using the same amount of cells, the novel use allows for producing a 10-times higher amount of viruses and thus also a 10-times higher amount of vaccine. Therewith, the time needed for producing a sufficiently high amount of vaccine is significantly reduced so that it is possible to react on epidemic diseases much more quickly and flexible than so far.

Since the cell lines, the use of which is presently claimed, are avian epithelial cell lines, they have the potential to act as natural host cells for avian viruses such as influenza viruses. Fresh virus isolates of newly occurring pandemic zoonoses of viruses having an avian origin can thus be easily propagated in these cell lines. In case of cell lines known from prior art to be used for vaccine production (such as canine or human cell lines) or in case of embryonated chicken eggs, the virus stems to be propagated need to be regularly adjusted to the host system. This cannot be successfully done in all cases. Thus, the specific cell lines referred to in the present application are particularly efficient in propagating new virus isolates that originate from birds or have been passed by birds.

The cell cultures referred to above originate from different gut sections of 18 days old chicken embryos. It was possible to passage the cells in vitro almost without limitation. It was further possible to biochemically characterize the cell lines as epithelial cells.

It was possible to produce both viruses able to cause an infection in fowl (also referred to as avian viruses) and viruses able to cause an infection in humans (also referred to as human viruses) in the cell lines; no significant difference in the efficiency of virus production could be observed.

In an embodiment, the produced viruses are human viruses. Vaccines against human viral diseases are of particular medical and economic importance. A simple and cost-effective production of high amounts of viruses to produce vaccines is a very efficient tool to fight against epidemic or pandemic outbreaks of diseases.

In another embodiment, the viruses are avian viruses. Water birds, in which many different influenza viruses with all conceivable combinations of subtypes of the viral surface antigens hemagglutinin (HA) and neuraminidase (NA) circulate, constitute a highly relevant virus reservoir. From there, the viruses occasionally reach poultry flocks where they can mutate into a highly pathogenic form (avian influenza). The avian viruses can then be transmitted to humans. Infection occurs either directly from infected poultry or via a detour through the pig, which acts as a "mixing vessel" for avian and human influenza viruses. If the viruses then acquire the ability to be transmitted from person to person, a worldwide pandemic can develop. Therefore, it might be very helpful to fight against such diseases by vaccination of poultry on the basis of avian viruses.

In an embodiment, the viruses are chosen from the group consisting of influenza virus, avian infectious bronchitis virus, avian infectious laryngotracheitis virus, avian nephritis virus, chicken anemia virus, egg drop syndrome virus, infectious bursal disease virus, Marek's disease virus, and Newcastle disease virus (NDV).

Thereby, the Newcastle disease virus is of particular interest since a vaccination against the Newcastle disease is mandatory for poultry stocks within the European Union. The Newcastle disease virus has a worldwide occurrence and is able to eliminate a complete poultry stock within two days.

In an embodiment, the viruses are viruses belonging to the family of orthomyxoviridae. Influenza virus A, influenza virus B, influenza virus C, influenza virus D, isavirus, thogotovirus, and quaranjavirus are typical viruses belonging to that family.

In an embodiment, the viruses are influenza viruses. Influenza is one of the most dangerous and fatal diseases the human is confronted with. Therefore, highly efficient techniques for producing vaccines against influenza are of utmost importance.

In an embodiment, the viruses belong to any of the following strains or lines or are genetically similar to viruses of the following strains or lines: A/Michigan/45/2015 (H1N1) pdm09, A/Singapore/INFIMH-16-0019/2016 (H3N2), A/FPV/Rostock/1934, A/WSN/1933, B/Colorado/06/2017, B/Victoria/2/87, B/Phuket/3073/2013, B/Yamagata/16/88. A virus is considered to be genetically similar to another virus if the sequence of its genetic material, i.e. its genome, (in particular its RNA) is at least 90%, in particular at least 91%, in particular at least 92%, in particular at least 93%, in particular at least 94%, in particular at least 95%, in particular at least 96%, in particular at least 97%, in particular at least 98%, in particular at least 99%, in particular at least 99.5%, in particular at least 99.9% identical to the sequence of the genetic material of the other virus.

In an embodiment, the viruses are viruses chosen from the group comprising or consisting of influenza subtype viruses, in particular influenza A subtype viruses, H1N1, H1N2, H2N2, H2N3, H3N1, H3N2, H3N8, H5N1, H5N2, H5N3, H5N6, H5N8, H5N9, H6N1, H6N2, H7N1, H7N2, H7N3, H7N4, H7N7, H7N9, H9N2, H10N7, and H10N8.

In an embodiment, the viruses are influenza viruses able to cause an infection in at least one of humans, fowl, seals, pigs, cattle, dogs, and horses. In an embodiment, the viruses are influenza viruses able to cause an infection in fowl or birds (avian influenza viruses) or influenza viruses able to cause an infection in humans (human influenza viruses). As explained above, the origin of many human influenza viruses can be found in poultry stocks. Therefore, a proper vaccination against avian influenza viruses can significantly reduce the risk of the occurrence of novel influenza viruses being dangerous for humans.

In an aspect, the proposed solution relates to a method for manufacturing viruses in an in vitro cell culture. This manufacturing method comprises the steps explained in the following.

First, a cell culture of avian epithelial cells is provided. Thereby, these avian epithelial cells are chosen from at least one of the cell cultures deposited under deposition numbers DSM ACC3345, DSM ACC3346, DSM ACC3347, DSM ACC3348, DSM ACC3349 at Leibniz-Institut DSMZ-Deutsche Sammlung von Mikroorganismen and Zellkulturen GmbH on Dec. 12, 2018.

Afterwards, virus particles are added to the cell culture. This induces an infection of at least some of the cells in the cell culture with virus particles. Since the viruses are reproduced within the cells to a high amount and afterwards released to the cell medium, an infection of almost all the cells in the cell culture typically occurs.

After the initial infection, the cells are incubated for first period of time to allow sufficient virus growth within the cells.

The viruses are excreted by the cells to the cell medium (i.e., the supernatant of the cell culture). Therefore, in another method step, the viruses produced by the cell culture are recovered from the supernatant (cell medium) of the cell culture.

In an embodiment, the cell medium comprises trypsin. In an embodiment, an infection medium in which the virus particles are added to the cell medium comprises trypsin. In an embodiment, the trypsin concentration in the cell medium and/or in the infection medium lies in a range of 0.1 µg/ml to 10 µg/ml, in particular 0.2 µg/ml to 9 µg/ml, in particular 0.3 µg/ml to 8 µg/ml, in particular 0.4 µg/ml to 7 µg/ml, in particular 0.5 µg/ml to 6 µg/ml, in particular 0.6 µg/ml to 5 µg/ml, in particular 0.7 µg/ml to 4 µg/ml, in particular 0.8 µg/ml to 3 µg/ml, in particular 0.9 µg/ml to 2 µg/ml, in particular 1.0 µg/ml to 1.5 µg/ml.

In an embodiment, the step of infecting the cells is done with a concentration of 0.00001 to 10 virus particles per cell in the cell culture, in particular with a concentration of 0.0001 to 5 virus particles, in particular with 0.001 to 2.5 virus particles, in particular with 0.01 to 1.5 virus particles, in particular with 0.1 to 1 virus particles per cell in the cell culture.

To allow for good virus reproduction, the step of incubating the cells is, in an embodiment, done at a temperature of 32° C. to 45° C., in particular of 33° C. to 44° C., in particular of 34° C. to 43° C., in particular 35° C. to 42° C., in particular 36° C. to 41° C., in particular 37° C. to 40° C., in particular 38° C. to 39° C. Such an incubation temperature resembles the native growth temperature of the cells and thus allows for a particular strong virus growth in the cells.

In an embodiment, the first period of time has a duration of between 24 hours and 1 week, in particular between 48 hours and 6 days, in particular between 60 hours and 5 days, in particular between 3 days and 4 days. After that time period, a sufficient amount of viruses has been produced, whereas the share of viable cells in the cell culture is significantly reduced due to the high virus load.

In an embodiment, the viruses recovered from the supernatant of the cell culture is concentrated and/or purified. For this purpose, centrifugation techniques like ultracentrifugation of filtration techniques are particularly appropriate.

In an aspect, the proposed solution relates to a method for manufacturing a vaccine. This manufacturing method comprises the steps explained in the following.

In a first step, a virus culture that has been obtained by the above explained use or by the above explained method of producing viruses in a cell culture is provided.

Alternatively, the above explained method of producing viruses in a cell culture is carried out to obtain a virus culture.

Afterwards, the viruses contained in the virus culture are inactivated or attenuated. Additionally or alternatively, they are fragmented. An antigen solution comprising inactivated, attenuated and/or fragmented virus particles results.

This antigen solution is then combined with at least one carrier substance and optionally further substances like adjuvants to obtain a vaccine. In contrast to prior art techniques, it is no longer necessary to rely on embryonated eggs for producing viruses used as main pharmaceutically active ingredient of the vaccine. Rather, the presently claimed vaccine manufacturing method does not make use of such embryonated eggs.

In an embodiment, the virus culture and/or the antigen solution is concentrated and/or purified to obtain a processed virus culture and/or a processed antigen solution. The processed virus culture comprises viruses in a defined concentration and/or purity. Likewise, the processed antigen solution comprises antigens in a defined concentration and/or purity.

Many vaccines comprise viruses of different virus strains in order to enhance the overall effectiveness of the vaccine. Therefore, in an embodiment, at least two different virus cultures comprising different virus strains are used for manufacturing the vaccine. To give an example, at least or exactly 2, 3, 4, 5, 6, 7, 8, 9, or 10 different virus cultures comprising different virus strains can be combined in order to manufacture a highly effective vaccine. Typically, 2, 3, or 4 different virus strains are combined in case of an anti-influenza vaccine.

All details, aspect and embodiments explained with respect to the novel use of cells can be combined in any desired way and can be transferred to the described manufacturing methods, and vice versa. Furthermore, details, aspects and embodiments of one of the described manufacturing methods can be transferred in any desired combination to the respective other manufacturing method, and vice versa.

BRIEF DESCRIPTION OF THE DRAWINGS

Further details of aspects of the proposed solution will be explained with respect to exemplary embodiments and accompanying Figures.

DETAILED DESCRIPTION

FIGS. 1A to 3B will be explained in connection with an exemplary embodiment in which all cell cultures of different continuously (permanently) growing avian cell lines derived from chicken gut were grown and infected with two influenza A virus strains under identical conditions.

Briefly, adherent immortalized epithelial cell lines from chicken intestine (cell clones deposited under accession numbers DSM ACC3345, DSM ACC3346, DSM ACC3347, DSM ACC3348, DSM ACC3349 at Leibniz-Institut DSMZ-Deutsche Sammlung von Mikroorganismen und Zellkulturen GmbH on Dec. 12, 2018), and also epithelial Madin Darby canine kidney cells (MDCK II cells), which were used as reference cell line, were routinely maintained in growth medium (Dulbecco's Modified Eagle Medium (DMEM) supplemented with 10% (v/v) fetal bovine serum (FCS), 100 U/ml penicillin and 0.1 mg/ml streptomycin) under standard cell culture conditions (humidified atmosphere with 5% $CO_2$ at 37° C.). Cells were passaged every 3 to 7 days when reaching confluency.

For infection, the cells were seeded into 6-well polystyrene cell culture plates (8.9 $cm^2$/well) one day prior to infection and grown to 90-100% confluency. Virus stocks were diluted in infection medium (DMEM with 0.1% (v/v) FCS, 0.2% bovine serum albumin (BSA), 100 U/ml penicillin, 0.1 mg/ml streptomycin, and 2 µg/ml trypsin treated with tosyl phenylalanyl chloromethyl ketone (TPCK)) and incubated on the cells for 1 h a 37° C. Infection was performed with a multiplicity of infection (MOI) of 0.00001. The cells were washed once with Dulbecco's phosphate buffered saline (DPBS) and finally incubated with infection medium at 37° C. Aliquots of 200 µl were taken at the respective time points post-infection. Virus titers were determined by plaque assay as the concentrations of plaque forming units (PFU) per milliliter.

Growth curves were monitored for a low-pathogenic variant of avian Influenza A/FPV/Rostock/1934 (H7N1) virus (FPV) and for human-derived Influenza A/WSN/1933 (H1N1) virus (WSN).

Figure 1A:
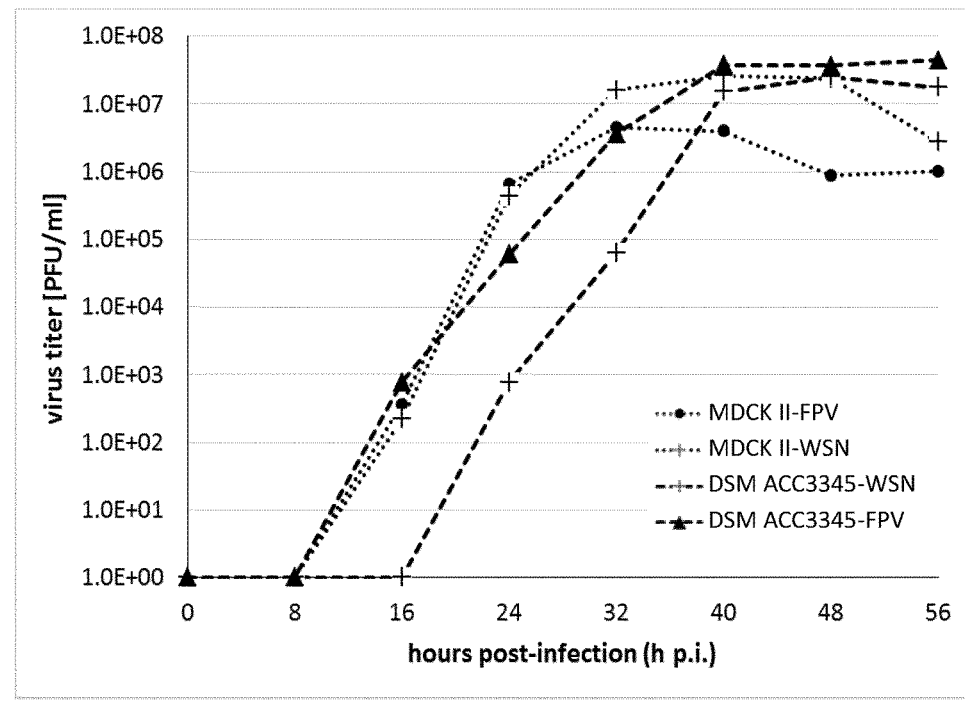
FIG. 1A shows a plot on the obtained virus titer in a first avian epithelial cell culture in comparison to the obtained virus titer in MDCK cells.
Figure 1B:
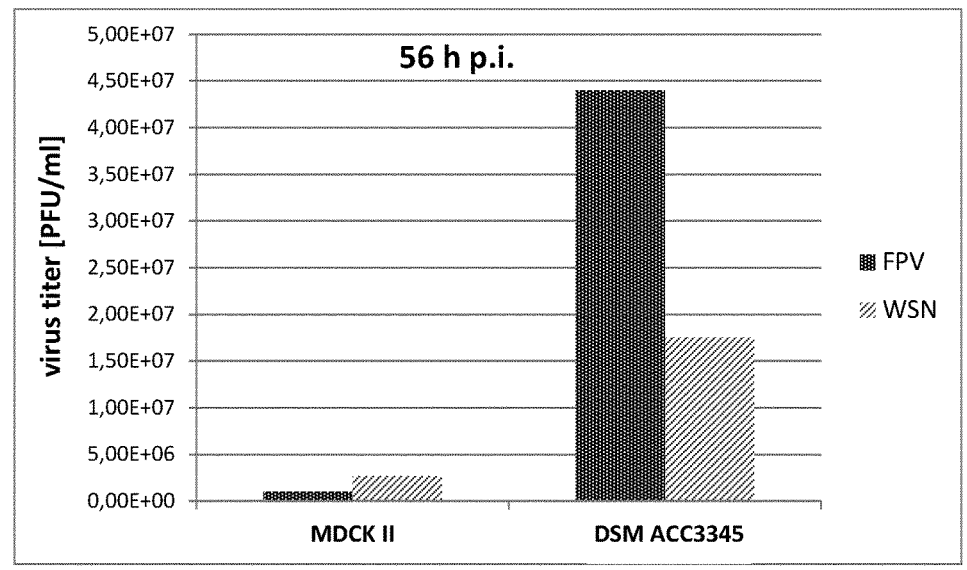
FIG. 1B shows the final virus titer obtained in the cell cultures of FIG. 1A 56 hours after infection.
Figure 2A:
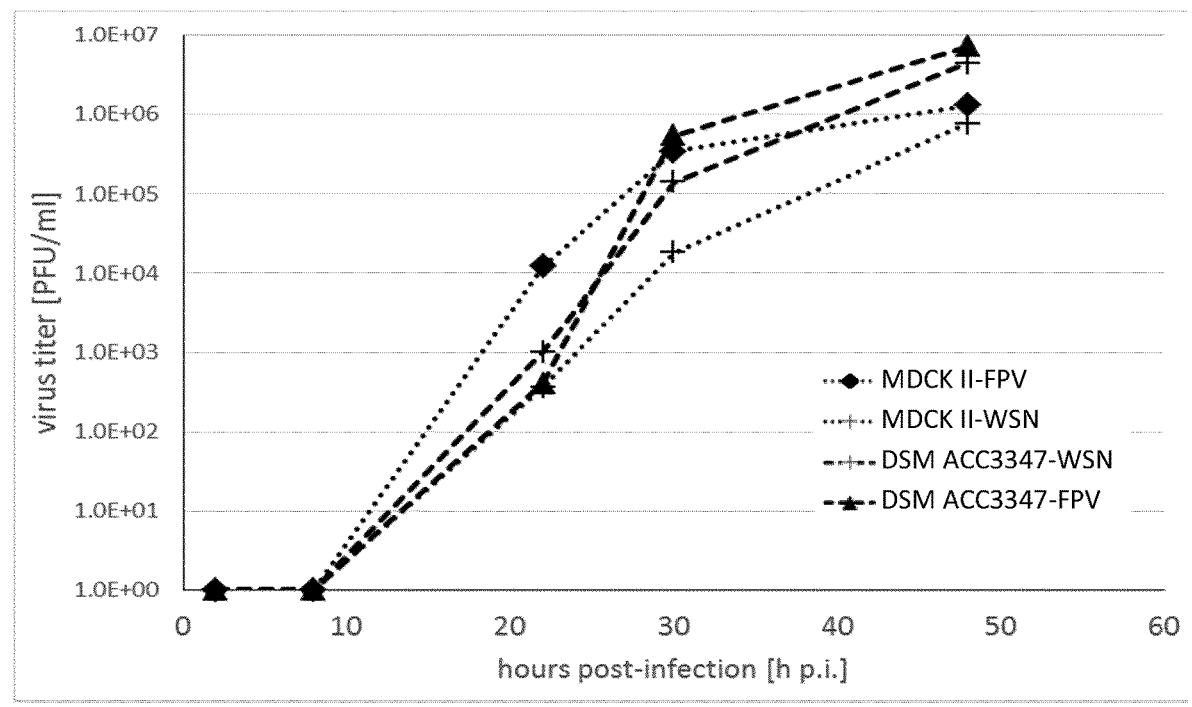
FIG. 2A shows a plot on the obtained virus titer in a second avian epithelial cell culture in comparison to the obtained virus titer in MDCK cells.
Figure 2B:
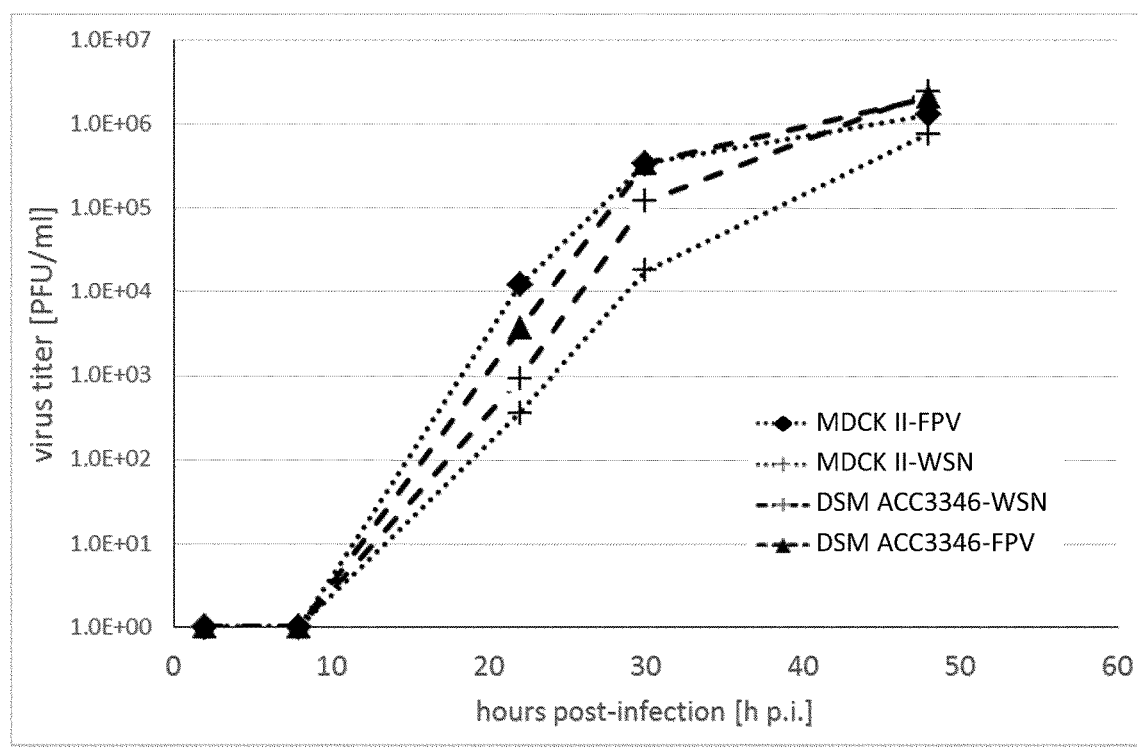
FIG. 2B shows a plot on the obtained virus titer in a third avian epithelial cell culture in comparison to the obtained virus titer in MDCK cells.
Figure 2C:
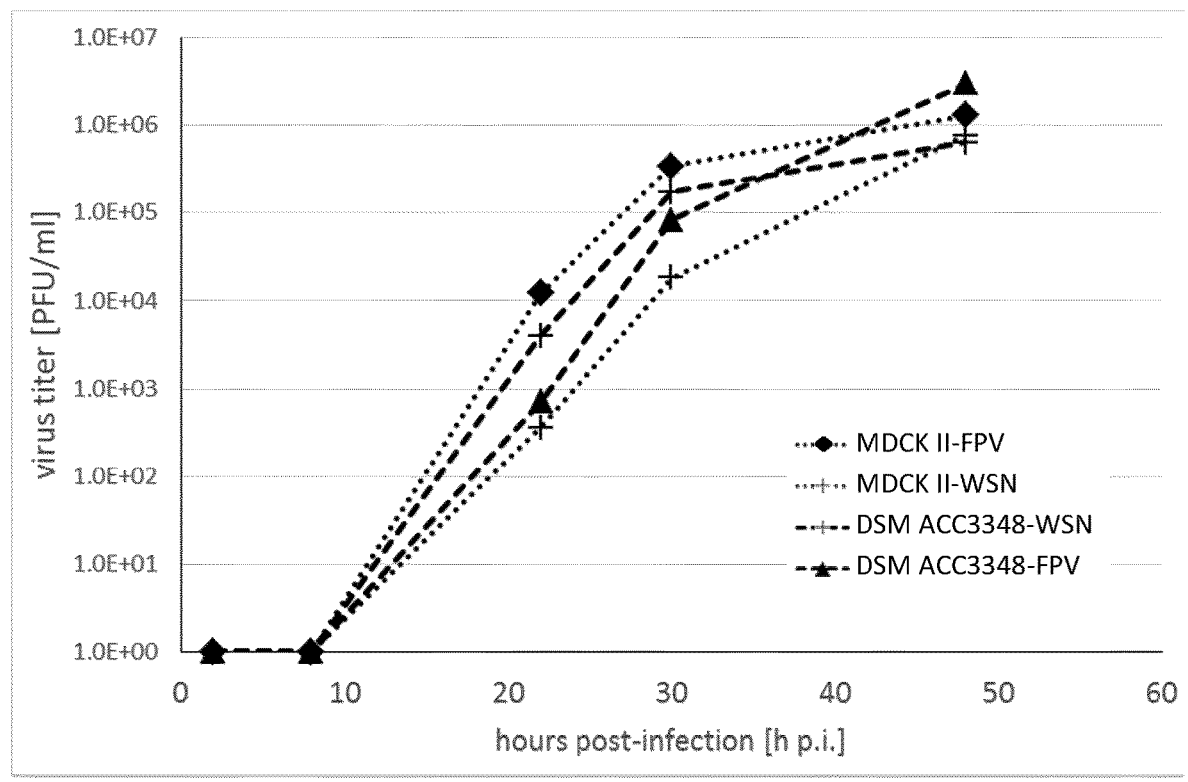
FIG. 2C shows a plot on the obtained virus titer in a forth avian epithelial cell culture in comparison to the obtained virus titer in MDCK cells.
Figure 2D:
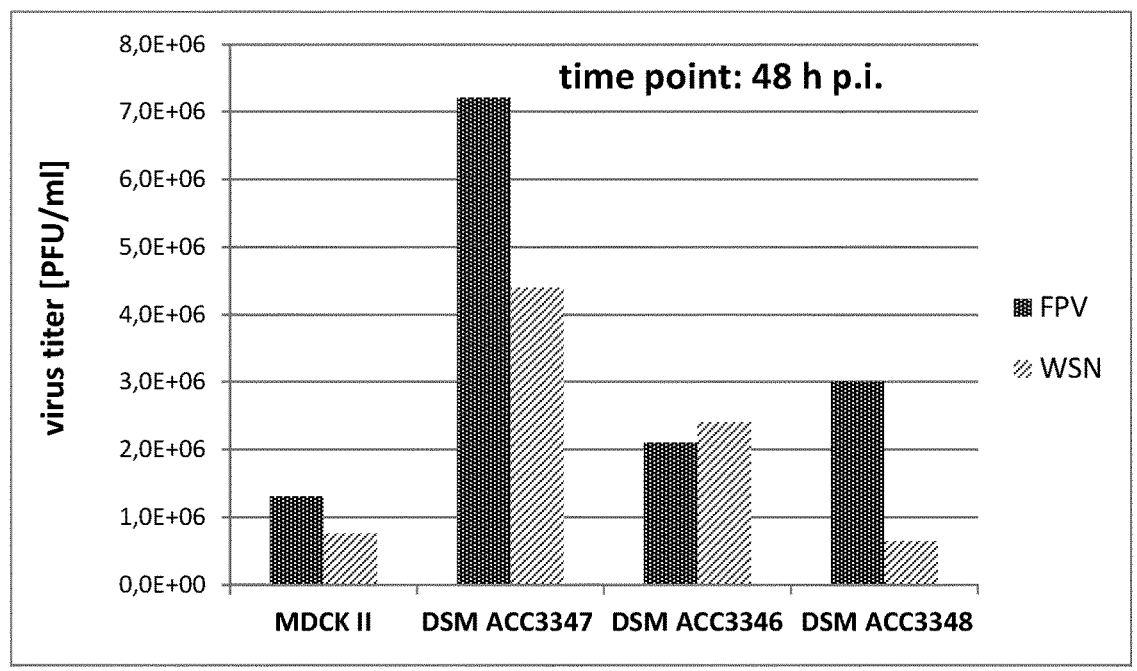
FIG. 2D shows the final virus titer obtained in the cell cultures of FIGS. 2A to 2C 48 hours after infection.

FIGS. 1A and 1B show that both FPV viruses and WSN viruses grow in the avian endothelial cell culture DSM ACC3345 to a much higher extent than in "classic" MDCK II cells. At 56 hours after the infection of the respective cells with the viruses, the virus titer is in the used avian endothelial cells more than 14 times higher than in case of MDCK II cells for FPV viruses. For WSN viruses, the virus titer is still more than 5 times higher in case of the chosen avian endothelial cells than in case of MDCK II cells.

FIGS. 2A to 2D show similar results for the avian endothelial cell cultures DSM ACC3346, DSM ACC3347 and DSM ACC3348 both in case of FPV viruses and in case of WSN viruses. At 48 hours after infection, the virus titer could be approximately doubled in DSM ACC3346 cells with respect to MDCK II cells in case of FPV viruses. It could even be roughly tripled in DSM ACCC3348 cells and was in DSM ACC3347 cells almost 7 times as high as in MDCK II cells. The virus growth of WSN cells in DSM ACC3348 a cells was approximately the same as in MDCK II cells, wherein it was 2 times higher in DSM ACC3346 cells and more than 4 times higher in DSM ACC3347 cells.

Figure 3A:
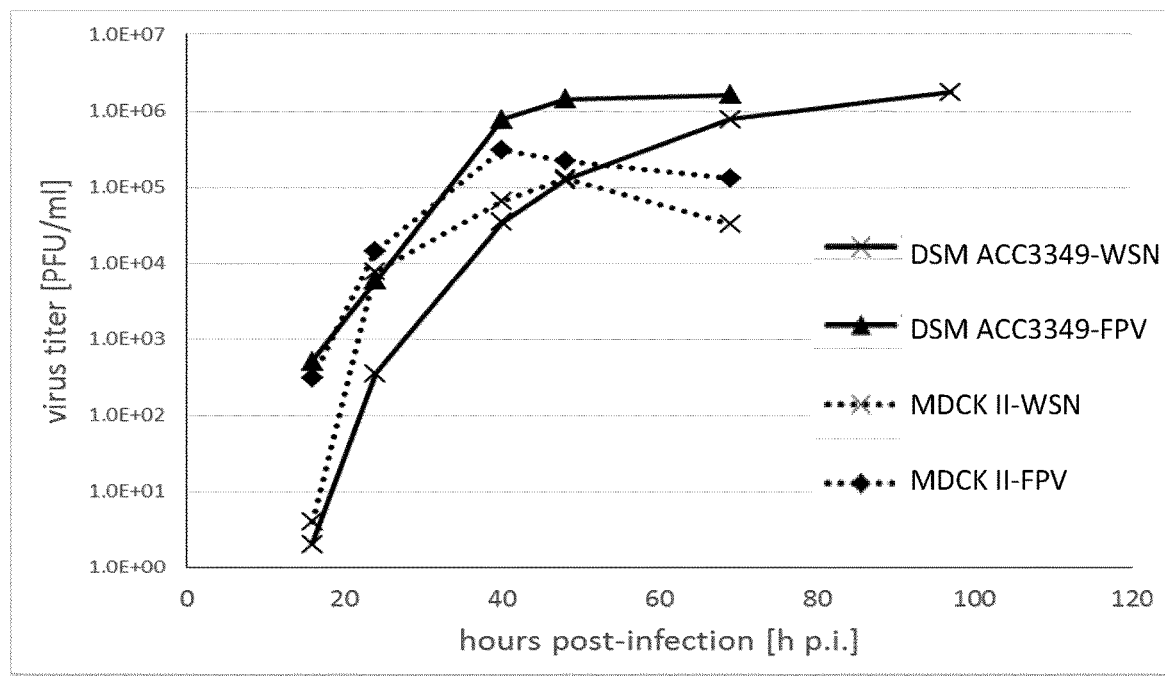
FIG. 3A shows a plot on the obtained virus titer in a fifth avian epithelial cell culture in comparison to the obtained virus titer in MDCK cells.
Figure 3B:
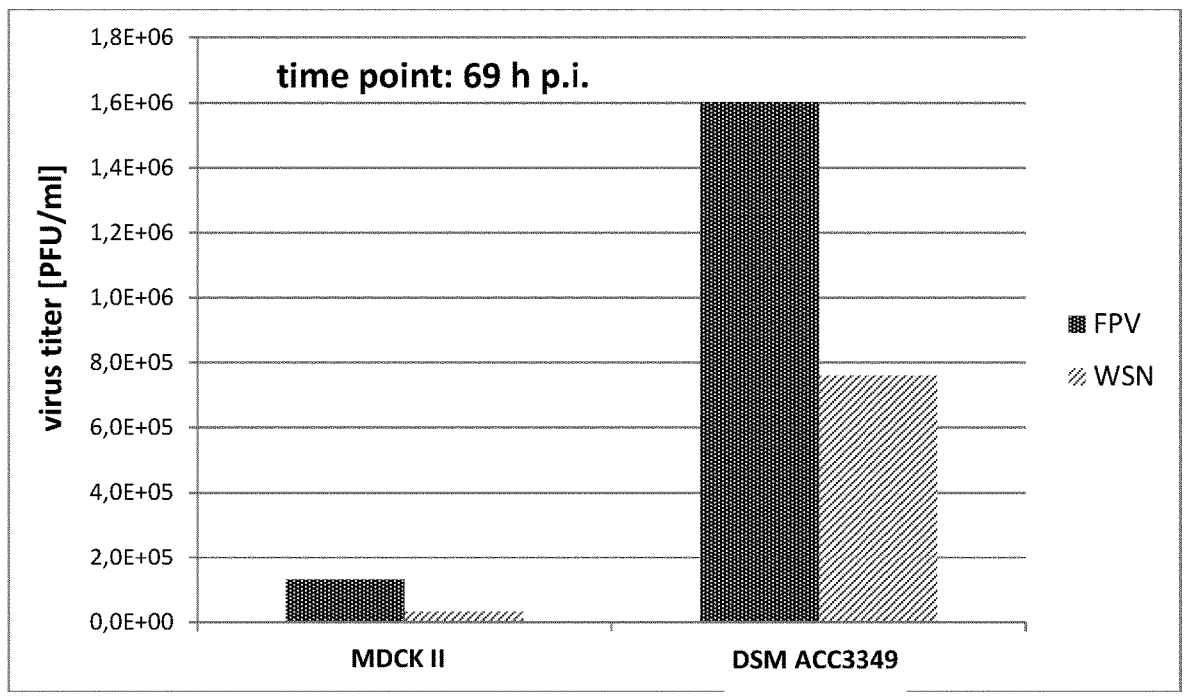
FIG. 3B shows the final virus titer obtained in the cell cultures of FIG. 3A 69 hours after infection.

A very high virus growth of FPV viruses and WSN viruses could also be observed in avian endothelial cells of the DSM ACC3349 cell culture, as can be seen from FIGS. 3A and 3B. At 69 hours after infection, the virus titer of FPV viruses was in DSM ACC3349 cells more than 8 times higher than in MDCK II cells. The virus titer of WSN viruses was in DSM ACC3349 cells even more than 10 times higher than in MDCK II cells.

The results presented in the Figures clearly show that the avian endothelial cell lines deposited under accession numbers DSM ACC3345, DSM ACC3346, DSM ACC3347, DSM ACC3348, DSM ACC3349 at Leibniz-Institut DSMZ-Deutsche Sammlung von Mikroorganismen und Zellkulturen GmbH on Dec. 12, 2018 show a significant better virus growth than MDCK II cells used according to prior art for producing influenza viruses in vitro. Thus, the cell cultures are particularly appropriate to be used for manufacturing viruses, in particular influenza viruses to be used, e.g., for vaccination purposes.

Figure 4:
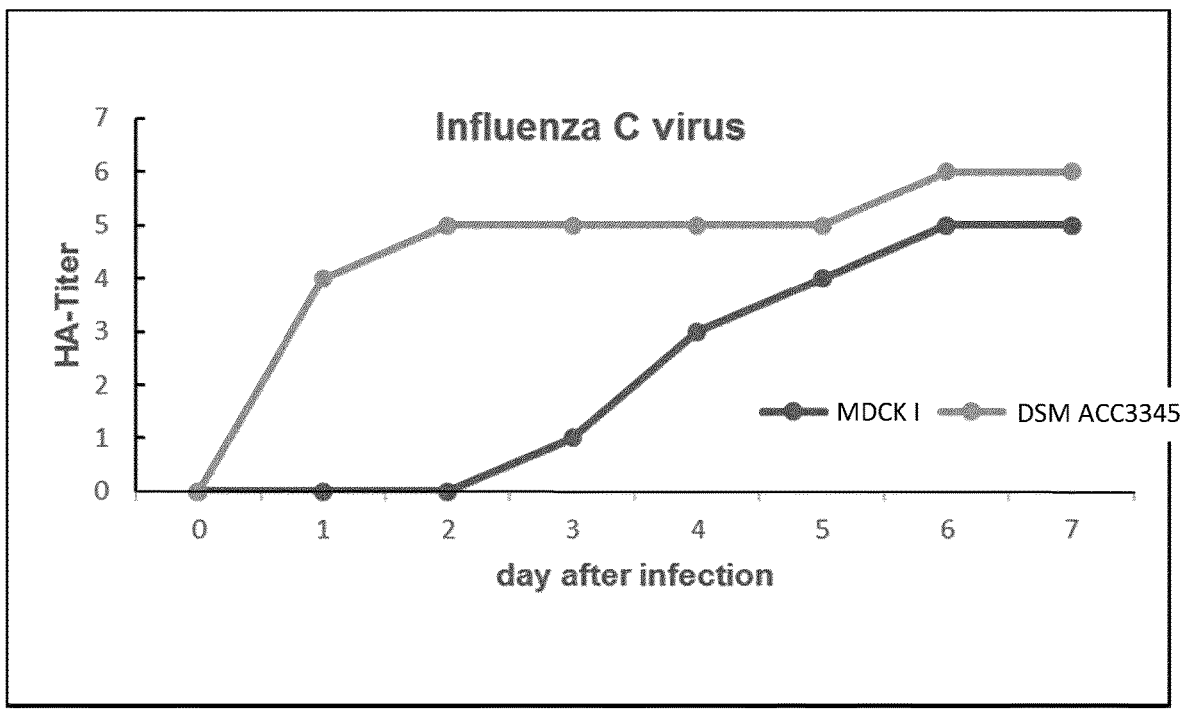
FIG. 4 shows a plot on the obtained virus titer of influenza C viruses in a further avian epithelial cell culture in comparison to the obtained virus titer in MDCK cells.
Figure 5:
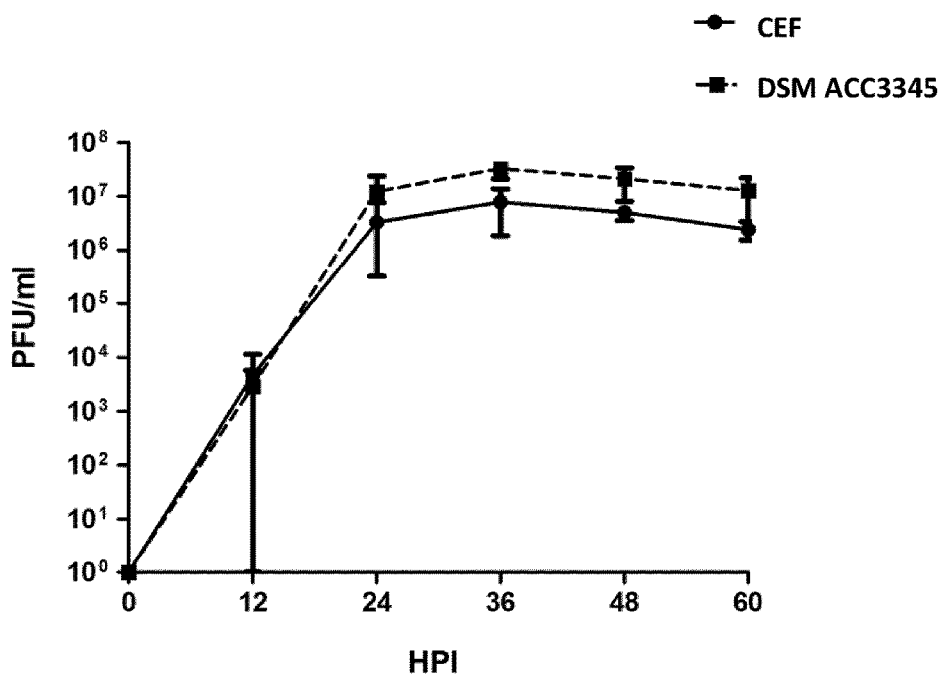
FIG. 5 shows a plot on the obtained virus titer of Newcastle disease viruses in a further avian epithelial cell culture in comparison to the obtained virus titer in chicken embryo fibroblast cells.

FIGS. 4 and 5 show the results of further virus growth experiments performed in DSM ACC3345 cells using influenza C virus and Newcastle disease virus. The cells were cultured as explained above with respect to FIGS. 1 to 3B. Likewise, the virus growth experiments were generally performed in the same way as the experiments explained with respect to FIGS. 1 to 3 B.

FIG. 4 shows the results of a virus infection with influenza C virus in DSM ACC3345 cells (grey line) and MDCK cells (black line). The cells were infected with influenza C virus strain JJ/50 at an MOI of 0.00005 and incubated in the presence of trypsin. At the indicated time points aliquots of the supernatant were removed and hemagglutinin titers (HA titers) were determined to evaluate virus growth. As indicated in FIG. 4, virus growth was much higher in DSM ACC3345 cells than in MDCK cells already at an early time point after infection. Furthermore, the final virus titer obtained in DSM ACC3345 cells was significantly higher than the final virus titer obtained in MDCK cells. Thus, influenza C virus can be very well grown in DSM ACC3345 cells. These cells present a particular appropriate vehicle for growing cells in vitro, e.g., for producing vaccines.

FIG. 5 shows the results of a virus infection with Newcastle disease virus (NDV) in DSM ACC3345 cells (dashed line) and chicken embryo fibroblast cells (CEF, solid line). The cells were infected with NDV strain Italian at an MOI of 0.00005 and incubated in the absence of trypsin. At the indicated time points (hours post infection, HPI) aliquots of the supernatant were removed and plaque titers were determined. Results are shown as the mean including standard deviation of two experiments.

Already 24 hours after infection, the virus growth in DSM ACC3345 cells is higher than the virus growth in CEF cells and remains at the higher level even within up to 60 hours after infection. Thus, NDV can be very well grown in DSM ACC3345 cells. These cells present a particular appropriate vehicle for growing cells in vitro, e.g., for producing vaccines.

The invention claimed is:

1. A method for manufacturing viruses in an in vitro cell culture, comprising the following steps: a) providing a cell culture of avian epithelial cells chosen from at least one of the cell cultures deposited under deposition numbers DSM ACC3345, DSM ACC3346, DSM ACC3347, DSM ACC3348, DSM ACC3349; b) infecting at least some of the cells in the cell culture with virus particles; c) incubating the cells for a first period of time; and d) recovering viruses produced by the cell culture from a supernatant of the cell culture.

2. The method according to claim 1, wherein the viruses are viruses able to cause an infection in humans.

3. The method according to claim 1, wherein the viruses are viruses able to cause an infection in fowl.

4. The method according to claim 1, wherein the viruses are chosen from the group consisting of influenza virus, avian infectious bronchitis virus, avian infectious laryngotracheitis virus, avian nephritis virus, chicken anemia virus, egg drop syndrome virus, infectious bursal disease virus, Marek's disease virus, and Newcastle disease virus.

5. The method according to claim 1, wherein the viruses are viruses belonging to the family of Orthomyxoviridae.

6. The method according to claim 1, wherein the viruses are influenza viruses.

7. The method according to claim 6, wherein the viruses are influenza viruses able to cause an infection in at least one of humans, fowl, seals, pigs, cattle, dogs, and horses.

8. The method according to claim 1, wherein the step of infecting is done with 0.00001 to 10 virus particles per cell in the cell culture.

9. The method according to claim 1, wherein the step of incubating is done at a temperature of 32° C. to 45° C.

10. The method according to claim 1, wherein the first period of time has a duration of between 24 hours and 1 week.

11. A method for manufacturing a vaccine, comprising the following steps:
a) carrying out a method according to claim 1 to obtain a virus culture;
b) inactivating or attenuating viruses contained in the virus culture and/or fragmenting viruses contained in the virus culture to obtain an antigen solution;
c) combining the antigen solution with a carrier substance to obtain a vaccine.

12. The method according to claim 11, wherein the virus culture and/or the antigen solution is concentrated and/or purified to obtain a processed virus culture comprising viruses in a defined concentration and/or purity and/or a processed antigen solution comprising antigens in a defined concentration and/or purity.

13. The method according to claim 11, wherein at least two different virus cultures comprising different virus strains of the same virus are used.

* * * * *